(12) United States Patent
Gareau et al.

(10) Patent No.: US 8,617,610 B2
(45) Date of Patent: Dec. 31, 2013

(54) COMPOSITIONS AND METHODS FOR INCREASING THE STABILITY OF FOOD PRODUCT ADDITIVES

(75) Inventors: Amber Lynn Gareau, Dartmouth (CA); Sharon Ann Spurvey Pittman, Middle Sackville (CA); Lariza Beristain Taboada, Dartmouth (CA)

(73) Assignee: DSM Nutritional Products AG, Kaiseraugst (CH)

( * ) Notice: Subject to any disclaimer, the term of this patent is extended or adjusted under 35 U.S.C. 154(b) by 0 days.

(21) Appl. No.: 13/476,231

(22) Filed: May 21, 2012

(65) Prior Publication Data

US 2013/0309313 A1   Nov. 21, 2013

(51) Int. Cl.
*A61K 31/202* (2006.01)
*A61K 9/50* (2006.01)
*A61K 9/107* (2006.01)
*A61K 31/232* (2006.01)
*A61P 9/00* (2006.01)

(52) U.S. Cl.
USPC ........... 424/492; 424/400; 424/490; 424/491; 424/493; 424/494; 514/560; 514/549

(58) Field of Classification Search
None
See application file for complete search history.

(56) References Cited

U.S. PATENT DOCUMENTS

| | | | |
|---|---|---|---|
| 6,969,530 B1 | 11/2005 | Curtis et al. | |
| 6,974,592 B2 | 12/2005 | Yan | |
| 7,727,629 B2 | 6/2010 | Yan | |
| 8,034,450 B2 | 10/2011 | Curtis et al. | |
| 2005/0019416 A1 | 1/2005 | Yan | |
| 2005/0095301 A1* | 5/2005 | Deshpande | 424/490 |
| 2005/0245612 A1* | 11/2005 | Blass | 514/560 |
| 2007/0269566 A1* | 11/2007 | Curtis et al. | 426/519 |
| 2010/0055281 A1 | 3/2010 | Barrow et al. | |
| 2010/0173002 A1* | 7/2010 | Yulai et al. | 424/492 |
| 2011/0117180 A1 | 5/2011 | Yan et al. | |

FOREIGN PATENT DOCUMENTS

| | | | | |
|---|---|---|---|---|
| EP | 1950210 | * | 1/2007 | .......... C07D 311/62 |
| EP | 1897530 A1 | | 3/2008 | |
| EP | 1950210 B1 | | 1/2013 | |
| KR | 20100027602 | * | 3/2010 | ............... A23L 1/29 |
| KR | 20100098807 A | | 9/2010 | |
| WO | 2004/041251 A1 | | 5/2004 | |
| WO | WO2007008384 | * | 1/2007 | ............... A23L 1/00 |
| WO | 2008/024906 A2 | | 2/2008 | |
| WO | 2008/043856 A1 | | 4/2008 | |

OTHER PUBLICATIONS

Lu et al., Quaity and anti-oxidant property of green tea sponge cake, Food Chemistry, 2010, vol. 119, pp. 1090-1095.*
Appel et al., Does supplementation of diet with 'fish oil' reduce blood pressure? A meta-analysis of controlled clinical trials, Arch. Intern. Med., 153(12):1429-1438 (1993).
Dyrberg et al., N-Omega-3 Fatty Acids: Prevention and Treatment of Vascular Disease, Kristensen et al., eds., Bi & Gi Publ., Verona-Springer-Verlag, London, pp. 217-226 (1995).
GISSI-Prevenzione Investigators, Dietary supplementation with omega-3 polyunsaturated fatty acids and vitamin E after myocardial infarction: Results of the GISSI-Prevenzione trial, Lancet, 354:447-455 (1999).
Harris, Extending the cardiovascular benefits of omega-3 fatty acids, Curr. Atheroscler. Rep, 7:375-380 (2005).
Holub, Clinical nutrition: 4 omega-3 fatty acids in cardiovascular care, Can. Med. Assoc. J., 166(5):608-615 (2002).
Kris-Etherton et al., Fish Consumption, Fish Oil, Omega-3 Fatty Acids and Cardiovascular Disease, Circulation, 106:2747-2757 (2002).
Muskiet et al., Is docosahexaenoic acid (DHA) essential? Lessons from DHA status regulation, our ancient diet, epidemiology and randomized controlled trials, J. Nut., 134(1):183-186 (2004).
O'Keefe et al., Omega-3 fatty acids: time for clinical implementation? Am. J. Cardiology, 85:1239-1241 (2000).
Radack et al., The effects of low doses of omega-3 fatty acid supplementation on blood pressure in hypertensive subjects: a randomized controlled trial, Arch. Intern. Med., 151:1173-1180 (1991).
Sugano, Balanced intake of polyunsaturated fatty acids for health benefits, J. Oleo Sci., 50(5):305-311 (2001).
Sunphenon® XLB-100, Decaffeinated Green Tea Extract Powder data sheet (Mar. 1, 2011).
Vitagreen TX-50, certificate of analysis data sheet (Sep. 15, 2009).
Webb, Alternative sources of omega-3 fatty acids, Natural Foods Merchandiser, XXVI(8):40-44 (2005).
International Search Report and Written Opinion for Application No. PCT/IB2012/00131 dated Jan. 21, 2013.
Teavigo Fact Sheet, www.centerchem.com, Feb. 1, 2012, pp. 1-2, XP055049144.

* cited by examiner

*Primary Examiner* — Daniel Sullivan
*Assistant Examiner* — Ping Cao

(57) ABSTRACT

Disclosed are compositions including powdered green tea extract and a powdered preparation comprising polyunsaturated fatty acids. Also disclosed are methods of preparing the compositions and using the compositions in food products, as well as food products containing or that are prepared from the compositions.

35 Claims, 2 Drawing Sheets

COMPOSITIONS AND METHODS FOR INCREASING THE STABILITY OF FOOD PRODUCT ADDITIVES

FIELD

The subject matter disclosed herein generally relates to compositions containing powdered green tea extract and powdered preparations comprising polyunsaturated fatty acids. Also, the subject matter disclosed herein generally relates to methods of preparing the compositions and using the compositions in food products, as well as food products containing or that are prepared from the disclosed compositions.

BACKGROUND

Polyunsaturated fatty acids (PUFAs), including omega-3, omega-6 and omega-9 fatty acids, are vital to everyday life and function. For example, the beneficial effects of omega-3 fatty acids like cis-5,8,11,14,17-eicosapentaenoic acid (EPA) and cis-4,7,10,13,16,19-docosahexaenoic acid (DHA) on lowering serum triglycerides are well established. All-cis-9,12,15-octadecatrienoic acid (ALA) is the precursor essential fatty acid of EPA and DHA. All-cis-5,8,11,14-eicosatetraenoic acid (AA) and its precursors all-cis-6,9,12-octadecatrienoic acid (GLA) and all-cis-9,12-octadecadienoic acid (LA) have been shown to be beneficial to infants.

Several of these compounds are also known for other cardioprotective benefits such as preventing cardiac arrhythmias, stabilizing atherosclerotic plaques, reducing platelet aggregation, and reducing blood pressure. See e.g., Dyrberg et al., In: Omega-3 Fatty Acids: Prevention and Treatment of Vascular Disease. Kristensen et al., eds., Bi & Gi Publ., Verona-Springer-Verlag, London, pp. 217-26, 1995; O'Keefe and Harris, *Am. J. Cardiology* 2000, 85:1239-41; Radack et al., "The effects of low doses of omega-3 fatty acid supplementation on blood pressure in hypertensive subjects: a randomized controlled trial." *Arch. Intern. Med.* 1991, 151:1173-80; Harris, "Extending the cardiovascular benefits of omega-3 fatty acids." *Curr. Atheroscler. Rep.* 2005, 7:375-80; Holub, "Clinical nutrition: 4 omega-3 fatty acids in cardiovascular care." *CMAJ* 2002, 166(5):608-15. Indeed, the American Heart Association has also reported that omega-3 fatty acids can reduce cardiovascular and heart disease risk. Other benefits of omega-3 fatty acids are those related to the prevention and/or treatment of inflammation and neurodegenerative diseases, and to improved cognitive development. See e.g., Sugano and Michihiro, "Balanced intake of polyunsaturated fatty acids for health benefits." *J. Oleo Sci.* 2001, 50(5):305-11.

The fatty acids EPA and DHA can be synthesized in the human body from ALA; however, the conversion rate from this precursor molecule is limited (Muskiet et al., "Is docosahexaenoic acid (DHA) essential? Lessons from DHA status regulation, our ancient diet, epidemiology and randomized controlled trials." *J. Nutr.* 2004, 134(1):183-6). Accordingly, EPA and DHA in the body are primarily derived from dietary sources (e.g., oily fish). Diets rich in fish oils are known to have many beneficial effects for heart disease, cancer, arthritis, allergies, and other chronic diseases. Epidemiological clinical trials have shown that increasing the dietary intake of omega-3 fatty acids, in the form of fish or of fish oil supplements, may reduce various risk factors associated with cardiovascular disease. See e.g., The American Heart Association, Scientific Statement, "Fish Consumption, Fish Oil, Omega-3 Fatty Acids and Cardiovascular Disease," November 2002; Appel et al., "Does supplementation of diet with 'fish oil' reduce blood pressure? A meta-analysis of controlled clinical trials." *Arch. Intern. Med.* 1993, 153(12): 1429-1438; GISSI-Prevenzione Investigators. "Dietary supplementation with omega-3 polyunsaturated fatty acids and vitamin E after myocardial infarction: results of the GISSI-Prevenzione trial." *Lancet* 1999, 354:447-55.

In addition to fish oil sources of EPA and DHA, these PUFAs, as well as ALA, AA and GLA, can be and are derived from microbial sources including, without limitation, *Mortiarella alpina* for ARA and various species of Thraustochytrids for DHA and EPA. Plants are now being modified genetically to include genes that produce various PUFAs in further efforts to reduce costs associated with commercial production of these oils.

Despite the strong evidence for the various benefits of PUFAs like EPA and DHA, the average daily consumption of these fatty acids by North Americans is estimated to be between 0.1 to 0.2 grams, compared to a suggested daily intake of 0.65 grams to confer benefit (Webb, "Alternative sources of omega-3 fatty acids." *Natural Foods Merchandiser* 2005, XXVI(8):40-4). Since altering dietary patterns of populations is difficult, some people do not like to eat fish, and the notion of consuming PUFAs derived from microbes has not achieved general acceptance, the supplementation of diets with PUFAs is an important approach to addressing this problem. Unfortunately, many PUFAs are sensitive to oxidation and can have unpleasant sensory properties.

In light of the health benefits of PUFAs, alternative methods of delivering PUFAs to a subject and methods for reducing the oxidation of PUFAs are needed. The subject matter disclosed herein addresses these and other needs.

SUMMARY

In accordance with the purposes of the disclosed materials, compounds, compositions, and methods, as embodied and broadly disclosed herein, the disclosed subject matter, in one aspect, relates to compositions that comprise a powdered green tea extract and a powdered preparation comprising PUFAs. In a further aspect, the disclosed subject matter relates to methods of preparing the compositions. In a still further aspect, the disclosed subject matter relates to food products comprising the compositions and methods of making the food products. Additional advantages will be set forth in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

DETAILED DESCRIPTION

Figure 1:
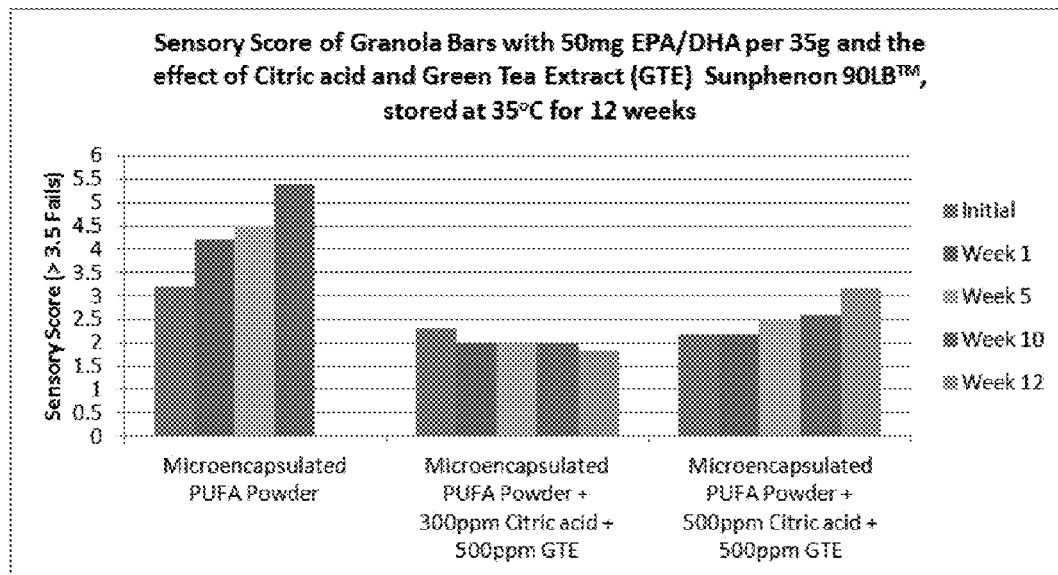
FIG. 1 is graph depicting sensory scores of granola bars prepared with microencapsulated PUFAs (which contained 50 mg EPA/DHA per 35 g of the granola bar) and varying amounts of citric acid and green tea extract after storing at 35° C. for twelve weeks. A sensory score of greater than 3.5 is considered failing.

The materials, compounds, compositions, and methods described herein can be understood more readily by reference to the following detailed description of specific aspects of the disclosed subject matter and the Examples and Figures included herein.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an antioxidant" includes mixtures of two or more such antioxidant, reference to "the polyunsaturated fatty acid" includes mixtures of two or more such polyunsaturated fatty acids, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. "About" can mean within 5% of the stated value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "5" is disclosed, then "about 5" is also disclosed.

References in the specification and concluding claims to parts by weight of a particular element or component in a composition denotes the weight relationship between the element or component and any other elements or components in the composition for which a part by weight is expressed. Thus, in a composition comprising 1 parts by weight of component X (e.g., the powdered green tea extract) and 10 parts by weight component Y (e.g., the powdered preparation comprising PUFAs), X and Y are present at a weight ratio of 1:10, and are present in such ratio regardless of whether additional components are comprised in the composition (e.g., the blend).

A weight percent (wt. %) of a component, unless specifically stated to the contrary, is based on the total weight of the formulation or composition in which the component is included.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), fish, and birds. "Subject" can also include a terrestrial or marine mammal, such as a whale, primate or a human.

Reference will now be made in detail to specific aspects of the disclosed materials, compounds, compositions, and methods, examples of which are illustrated in the accompanying Examples and Figures.

Materials and Methods

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Disclosed herein are compositions (also referred to as "blends") that comprise (i) a powdered green tea extract and (ii) a powdered preparation comprising PUFAs. By "powdered preparation comprising PUFAs" is meant a powdered emulsion or microcapsule that has a loading substance comprising one or more PUFAs. In the disclosed compositions, the powdered green tea extract and powdered preparation comprising PUFAs are, together, at least about 90% by weight of the composition, e.g., about 92, 94, 06, 98 or 100% by weight of the composition. Thus, the disclosed compositions can contain from about 0% to about 10% by weight of additional materials (i.e., materials other than the powdered green tea extract and powdered preparation comprising PUFAs) in the composition. Further, as is disclosed elsewhere herein, the disclosed compositions are particularly well suited to be used as ingredients in a wide variety of food products, such as granola bars.

Powdered Preparations Comprising PUFAs

Microcapsules

In certain aspects, the powdered preparation comprising PUFAs can be a microcapsule comprising one or more PUFAs as its core or loading substance. Suitable microcapsules for use in the disclosed compositions and methods are those that comprise an agglomeration of primary microcapsules and a loading substance, each individual primary microcapsule having a primary shell, wherein the loading substance is encapsulated by the primary shell, and wherein the agglomeration is encapsulated by an outer shell. Particularly suitable microcapsules are disclosed in U.S. Pat. Nos. 6,974,592, 6,969,530, 7,727,629, and 8,034,450, and US Publication Nos. 2005/0019416, 2010/0055281, 2010/0173002, and 2011/0117180, which are all incorporated by reference herein in their entireties for at least their disclosures of microcapsules, their methods of preparation, and their methods of use.

It is also contemplated that one or more additional shell layers can be placed on the outer shell of the microcapsules. The techniques described in International Publication No. WO 2004/041251, which is incorporated by reference in its entirety at least for its disclosure of microcapsules and their methods of preparation, can be used to add additional shell layers to the microcapsules.

In further examples, the primary shell and/or outer shell can be formed from a complex coacervate. A complex coacervate forms when two different polymer components (i.e., shell materials) come together through electrostatic interactions and form an insoluble complex or "complex coacervate" around droplets of loading substance. The complex coacervate that forms the primary shells can be different from the complex coacervate that forms the outer shell. In such a case, a polymer system that contains three or more different shell materials can be used to form the complex coacervate. In other examples, the same two shell materials (a two polymer component system) can be used to form both the primary and outer shells. For example, the primary shell and outer shell can be formed from a complex coacervate of gelatin and polyphosphate.

In such microcapsules, the shell material used to form the primary and/or outer shells can comprise a complex coacervate of gelatin and polyphosphate, gelatin and gum arabic, whey protein and gum arabic, and the like. Further examples of suitable materials for the primary shell and/or outer shells include, but are not limited to, complex coacervates of any one or more of the following proteins: gelatin type A, gelatin type B, pork gelatin, beef gelatin, fish gelatin, kosher gelatin, non-kosher gelatin, Halal gelatin, non-Halal gelatin, milk protein, casein, caseinate, whey protein, soy protein, pea protein, rice protein, canola protein, albumin, alfa-lactalbumin, beta-lactoglobumin, and ovalbumin, with one more of any of the following polymers: polyphosphate, gum arabic, gellan gum, xylan gum, agar, alginate, chitin, chitosan, carrageenan, pectin, starch, modified starch, polysorbiton, maltodextrin, cyclodextrin, cellulose, methyl cellulose, ethyl cellulose, hydropropylmethylcellulose, and carboxymethylcellulose.

In further examples, materials for the primary shell and/or outer shells can have a Bloom number of from about 0 to about 300, most preferably from about 200 to about 300. It is also contemplated that the shell material can have no Bloom number (0) or a low Bloom number of 1 to 50. The Bloom number describes the gel strength formed at 10° C. with a 6.67% solution gelled for 18 hours. Determining the Bloom number of a substance can be accomplished by methods known in the art. In some specific examples the primary shell and/or outer shell material can have a Bloom number of from about 0 to about 50, and in other examples the primary shell and/or outer shell material can have a Bloom number of from about 51 to about 300. Still other specific examples include microcapsules comprising a primary shell and/or outer shell material having a Bloom number of about 0, about 210, about 220, or about 240. It is contemplated that the primary shell and/or outer shell material can have a Bloom number of about 0, 10, 20, 30, 40, 50, 60, 70, 80, 90, 100, 110, 120, 130, 140, 150, 160, 165, 170, 180, 190, 200, 210, 220, 230, 240, 250, 260, 270, 280, 290, or 300, where any of the stated values can form an upper or lower endpoint of a range.

The outer shell of the microcapsules can have an average diameter of from about 1 μm to about 2,000 μm, from about 20 μm to about 1,000 μm, or from about 30 μm to about 80 μm. In further examples, the average diameter of the outer shell can be about 1, 10, 20, 30, 40, 50, 60, 70, 80, 90, 200, 300, 400, 500, 600, 700, 800, 900, 1000, 1200, 1300, 1400, 1500, 1600, 1700, 1800, 1900, or 2000 μm, where any of the stated values can form an upper or lower endpoint of a range. In preferred examples, the outer shell of the microcapsule can have an average diameter of less than about 500 μm, less than 200 μm, or less than about 100 μm.

The primary shells can have an average diameter of from about 40 nm to about 10 μm or from about 0.04 μm to about 5 μm. In further examples, the average diameter of the primary shell can be about 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm, 2 μm, 3 μm, 4 μm, or 5 μm, where any of the stated values can form an upper or lower endpoint of a range. In preferred examples, the primary shell can have an average diameter of less than Particle size of the primary and/or outer shell can be measured using any typical equipment known in the art, for example, a Coulter LS230 Particle Size Analyzer (Beckman Coulter; Miami, Fla.).

Emulsions

In other aspects, the powdered preparation comprising PUFAs can be a powered emulsion. The emulsions can comprise droplets of loading substance of various sizes and one or more polymer components, all in a powered form. For example, a suitable emulsion can be a microemulsion and/or a nanoemulsion. That is, the droplets of the emulsions can be in the micrometer range (i.e., 1 to 1000 μm) or nanometer range (i.e., 1 to 1000 nm, typically less than about 0.1 μm). Specific examples include, but are not limited to, emulsions that have an average droplet size of less than about 100, 90, 80, 70, 60, 50, 40, 30, 20, or 10 μm, where any of the stated values can form an upper or lower endpoint of a range. The size of the droplets of loading substance can be determined by methods known in the art, such as light scattering, microscopy, spectroscopically, and the like.

The polymer component for the emulsions can be any of the shell materials described herein in reference to the microcapsules. Specifically, the polymer component can comprise any one or more of the following: gelatin type A, gelatin type B, pork gelatin, beef gelatin, fish gelatin, kosher gelatin, non-kosher gelatin, Halal gelatin, non-Halal gelatin, milk protein, casein, caseinate, whey protein, soy protein, pea protein, rice protein, canola protein, albumin, alfa-lactalbumin, beta-lactoglobumin, ovalbumin, polyphosphate, gum arabic, gellan gum, xylan gum, agar, alginate, chitin, chitosan, carrageenan, pectin, starch, modified starch, polysorbiton, maltodextrin, cyclodextrin, cellulose, methyl cellulose, ethyl cellulose, hydropropylmethylcellulose, and carboxymethylcellulose, including any mixture or combination of these.

In one specific example of a suitable powered emulsion, the polymer component comprises gelatin.

Loading Substance

The powdered preparations comprising PUFAs, whether the microcapsule or emulsion, contains a loading substance that comprises one or more PUFAs and/or derivatives thereof. Derivatives of PUFAs can include alkyl esters (e.g., methyl or ethyl esters), glyceride esters (e.g., mono, di, and triacylglycerol), sterol esters (e.g., phytosterol or cholesterol esters), antioxidant esters (e.g., ascorbyl and citryl esters), furanoid esters, and salts of PUFAs (e.g., sodium, potassium, calcium, magnesium, and chromium salts). Any mixture or combination of PUFAs and/or derivatives thereof can also be suitable for use in the compositions and methods disclosed herein.

Particularly desirable PUFAs are omega-3 fatty acids. An omega-3 fatty acid is an unsaturated fatty acid that contains as its terminus $CH_3-CH_2-CH=CH-$. Generally, an omega-3 fatty acid has the following formula:

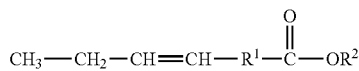

wherein $R^1$ is a $C_3$-$C_{40}$ alkyl or alkenyl group comprising at least one double bond and $R^2$ is H, metal, alkyl, glycerol, sterol, ascorbyl, citryl, or furanoidyl, group. The term "alkyl" as used herein is a saturated hydrocarbon group (e.g., methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like). The term "alkenyl" as used herein is a hydrocarbon group containing at least one carbon-carbon double bond. Asymmetric structures such as (AB)C=C(CD) are intended to include both the E and Z isomers (cis and trans). In a further example, $R^1$ can be a $C_5$-$C_{38}$, $C_6$-$C_{36}$, $C_8$-$C_{34}$, $C_{10}$-$C_{32}$, $C_{12}$-$C_{30}$, $C_{14}$-$C_{28}$, $C_{16}$-$C_{26}$, or $C_{18}$-$C_{24}$ alkenyl group. In yet another example, the alkenyl group of $R^1$ can have from 2 to 6, from 3 to 6, from 4 to 6, or from 5 to 6 double bonds. Still further, the alkenyl group of $R^1$ can have from 1, 2, 3, 4, 5, or 6 double bonds, where any of the stated values can form an upper or lower endpoint as appropriate. Specific examples of omega-3 fatty acids include, but are not limited to, those noted elsewhere herein.

In certain examples, the loading substance comprises DHA and/or EPA, a $C_1$-$C_6$ alkyl ester thereof, a triacylglycerol ester thereof, a phytosterol or cholesterol ester thereof, a salt thereof, and/or any mixture of one or more of these. Triacylglycerol oils (referred to as TG oils) can be used. Still further, the disclosed compositions and methods can use oils comprising re-esterified triglycerides.

The loading substance can be a solid, a liquid, or a mixture of a solid and a hydrophobic liquid, depending on the temperature and the particular PUFAs in the loading substance. Optionally, the loading substance can also comprise other biologically active substances, nutritional supplements, and/or flavorings, including any mixture or combination of these. In certain examples, the PUFA containing loading substance can be a microbial oil, algal oil (e.g., oil from a dinoflagellate such as *Crypthecodinium cohnii*), fungal oil (e.g., oil from *Thraustochytrium, Schizochytrium*, or a mixture thereof), and/or plant oil, including any mixture or combination of these.

In other examples, the loading substance can comprise a marine oil, such as natural, semi-refined, refined, concentrated, light pressed, alkali treated, heat treated, light brown, or heavy brown fish oil. Non-alkali treated fish oil is also a suitable loading substance. Fish oils come from a variety of sources. Examples of suitable fish oils include, but are not limited to, Atlantic fish oil, Pacific fish oil, Mediterranean fish oil, and any mixture or combination of these. More specific examples of suitable fish oils include, but are not limited to, bonito oil, pilchard oil, sea bass oil, halibut oil, spearfish oil, barracuda oil, cod oil, menhaden oil, sardine oil, anchovy oil, tuna oil, capelin oil, herring oil, mackerel oil, salmon oil, salmonid oil, and shark oil, including any mixture or combination of these.

While fish oils are most readily available, other marine oils can be suitable for use herein. Such marine oils include, but are not limited to, oil derived from marine mammals and/or marine invertebrates, including for example squid oil, octopus oil, krill oil, seal oil, whale oil, and the like, including any mixture or combination of these.

The loading substance can also comprise vegetable oils such as olive oil, corn oil, palm oil, sunflower oil, flaxseed, soybean oil, peanut oil, borage oil, primrose oil, linseed oil, rapeseed oil, and the like. Oils from plants that have been genetically modified to produce certain PUFAs can also be used. But in some examples, it is preferable that the PUFA is not a flax seed oil.

Suitable loading substances can also be referred to herein by the approximate ratio of EPA and DHA, or derivatives thereof, found in the loading substance. For example, 18:12 oils generally comprise a ratio of EPA to DHA (or their triglyceride esters for example) of about 18:12. Likewise, 5:25 oils generally comprise a ratio of EPA to DHA of about 5:25. Each of these types of oils can be used in the disclosed compositions and methods.

It is contemplated herein that one or more of any of the disclosed loading substances can be used. For example, the powdered preparation comprising PUFAs usable in the disclosed compositions and methods can contain two or more different loading substances, as disclosed herein. Further, the loading substance can be present in an amount of from about 10% to about 90% by weight of the powdered preparation comprising PUFAs. In specific examples, the loading substance can be present in an amount of from about 20% to about 80%, from about 30% to about 70%, from about 40% to about 60%, from about 50% to about 70%, or from about 60% to about 80% by weight of the powdered preparation comprising PUFAs.

Optionally, the loading substance can also contain an antioxidant. Suitable examples of antioxidants include, but are not limited to, a phenolic compound, a plant extract, or a sulphur-containing compound. In certain examples disclosed herein the antioxidant can be ascorbic acid or a salt thereof, e.g., sodium ascorbate. In other examples, the antioxidant can be citric acid or a salt thereof. In still other examples, the antioxidant can be vitamin E, $CoQ_{10}$, tocopherols, lipid soluble derivatives of more polar antioxidants such as ascorbyl fatty acid esters (e.g., ascorbyl palmitate), plant extracts (e.g., rosemary, sage and oregano oils), algal extracts, and synthetic antioxidants (e.g., BHT, TBHQ, ethoxyquin, alkyl gallates, hydroquinones, and tocotrienols).

The loading substance can also contain other nutrient(s) such as vitamins other trace elements, minerals, and the like. For example, the loading substance can contain one or more of a fat soluble vitamins (e.g., vitamins A, D, E, and K), tocotrienols, carotenoids, xanthophylls, (e.g., lycopene, lutein, astaxanthin, and zeazanthin), fat-soluble nutraceuticals including phytosterols, stanols and esters thereof, Coenzyme Q10, ubiquinol, hydrophobic amino acids, or an essential oil. Further, the powdered preparation comprising PUFAs can comprise other components such as preservatives, antimicrobials, chelating agents, thickeners, flavorings, diluents, emulsifiers, dispersing aids, or binders.

SPECIFIC EXAMPLES

Whether the powdered preparation comprising PUFAs is a microcapsule or powdered emulsion, it can comprise any of the shell materials and any of the loading substances disclosed herein. Some specific examples include, but are not limited to, microcapsules where the shell materials are formed from complex coacervates, e.g., complex coacervates of gelatin and polyphosphate. Similarly, powdered emulsions where the polymer component is gelatin and the loading substance is any of those disclosed herein. Loading substances that can be used in many examples include marine oils (e.g., fish oils and microbial oils). Loading substances that comprise PUFAs, such as EPA and DHA, are also desirable. Such microcapsules or emulsions can have at least about 130 mg of DHA or at least about 150 mg of EPA and DHA per gram of powder. Further, derivatives of omega-3 fatty acids, such as mono-, di-, and triglycerides, alkyl esters, sterol esters, antioxidant esters (e.g., ascorbyl and citryl esters), and furanoid esters, can also be suitable loading substances. In certain aspects, the powdered preparation comprising PUFAs can be a microencapsulated omega-3 fatty acid powder commercially available from Ocean Nutrition Canada Limited (Dartmouth, Canada) sold under the name MEG-3™.

The microcapsules can be prepared according to the methods described in U.S. Pat. Nos. 6,974,592, 6,969,530, 7,727, 629, and 8,034,450, and US Publication Nos. 2005/0019416, 2007/0269566, 2010/0055281, 2010/0173002, and 2011/0117180, which are incorporated by reference herein in their entireties for at least their disclosures of methods of preparing microcapsules. The microcapsules can be washed with water and dried to provide a free-flowing powder. Drying can be accomplished by a number of methods known in the art such as, for example, freeze drying, drying with ethanol, or spray drying. In one aspect, spray drying can be used for drying the microcapsules. Spray drying techniques are disclosed in "Spray Drying Handbook", K. Masters, 5th edition, Longman Scientific Technical UK, 1991, the disclosure of which is hereby incorporated by reference.

The emulsions can be prepared according to the methods described in US Publication No. 2010/0055281, which is incorporated by reference herein in its entirety for at least its disclosure of methods of preparing powdered emulsions. In general, the emulsions can be prepared by providing an aqueous mixture of the polymer component and a loading substance and emulsifying the mixture. Emulsifying the mixture can be accomplished by methods and apparatus known in the art, e.g., homogenization and high pressure/high shear pumps. For example, emulsification can take place by emulsifying at from about 1,000 to about 15,000 rpm. The emulsification step can be monitored by removing a sample of the mixture and analyzing it under such methods as microscopy, light scattering, turbidity, etc. Generally, emulsification can be performed until an average droplet size of less than about 1,000, 750, 500, 100, or 10 nm is obtained. It is further contemplated that antioxidants, which are also described herein, can be added to the aqueous mixture. Such antioxidants can be added before the emulsifying step, during the emulsifying step, and/or after the emulsifying step. It is also contemplated that after the emulsions are prepared, they are dehydrated. Methods for dehydrating emulsions are known in the art and include, but are not limited to, spray drying, freeze drying, evaporation, and the like.

Green Tea Extract

The compositions disclosed herein further contain a powdered green tea extract. The green tea extract is a component of the disclosed compositions, present in combination with the powdered preparation comprising PUFAs (microcapsules or emulsions). The green tea extract can also be part of the loading substance.

Green tea extracts suitable for use in the disclosed compositions include various components that have antioxidant activity, such as polyphenolic compounds (I.e., catechins). Examples of polyphenolic compounds that can be present in green tea extract include epigallocatechin gallate (EGCG), epigallocatechin (EGC), epicatechin gallate (ECG), epicatechin (EC), and mixtures of these. The green tea extracts that can be used in the disclosed compositions can have one or more polyphenolic compounds present in the extract in an amount from about 40 wt. % to about 90 wt. %, from about 45 wt. % to about 85 wt. %, from about 50 wt. % to about 80 wt. %, from about 60 wt. % to about 90 wt. %, from about 65 wt. % to about 85 wt. %, from about 70 wt. % to about 95 wt. %, from about 75 wt. % to about 90 wt. %, from about 80 wt. % to about 95 wt. %, or from about 85 wt. % to about 90 wt. % based on the weight of the green tea extract. Some preferred green tea extracts contain greater than about 80 wt. % polyphenols.

The green tea extracts that can be used in the disclosed compositions can have one or more catechins present in the extract in an amount from about 40 wt. % to about 80 wt. %, from about 45 wt. % to about 75 wt. %, from about 50 wt. % to about 70 wt. %, from about 55 wt. % to about 80 wt. %, from about 60 wt. % to about 75 wt. %, from about 65 wt. % to about 70 wt. %, from about 75 wt. % to about 80 wt. %, or from about 55 wt. % to about 65 wt. % based on the weight of the green tea extract. Some preferred green tea extracts can contain greater than about 60 wt. % catechins While not wishing to be bound by theory, it is believed that the content of the EGCG and the EGC impacts the ability of the disclosed compositions to provide compositions that have desirable sensory characteristics or stability. Green tea extracts suitable for use herein can have an epigallocatechin gallate (EGCG) content of greater than about 40 wt. %, greater than about 45 wt. %, greater than about 50 wt. %, or greater than about 55 wt. %, based on the weight of the green tea extract. For example, the green tea extract can have from about 40 to about 60 wt. % EGCG, from about 45 to about 55 wt. %, or about 50 wt. %, based on the weight of the green tea extract. The green tea extract can also have a epigallocatechin (EGC) content of from about 5 to about 20 wt. %, from about 5 to about 15 wt. %., from about 10 to about 13 wt. %, based on the weight of the green tea extract.

Still further, suitable green tea extracts for use herein can have a epicatechin (EC) content of greater than about 6 wt. %, from about 6 to about 15 wt. %, from about 6 to about 12 wt. %, from about 7 to about 10 wt. %, or from about 7 to about 9 wt. %, based on the weight of the green tea extract. Suitable green tea extracts for use herein can also have a epicatechin gallate (ECG) content of from about 2 to about 9 wt. %, from about 3 to about 8 wt. %, or from about 4 to about 7 wt. %, based on the weight of the green tea extract.

It is also desirable the green tea extracts be decaffeinated or have less than 1 wt. % caffeine.

The green tea extract is in the disclosed composition in a powdered form.

A commercially available powdered green tea extract that is suitable for use in the disclosed compositions and methods includes SUNPHENON 90LB™ and SUNPHENON 90D™ from Taiyo Kagaku Co. (Yokkaichi, Mie, Japan). Further examples of suitable green tea extracts include TEAVIGO™, commercially available from Pharmachem Laboratories, Inc. (Kearny, N.J.), and VITAGREEN TX50™ (VitaGreen Natural Green Tea Extract, commercially available from Vita Green, Hong Kong, CN). The green tea extracts suitable for use herein contain purified polyphenols. Still further examples of suitable green tea extracts include SUNPHENON XLB™ and SUNPHENON 90DCF-T™, both commercially available from Taiyo Kagaku Co. These green tea extracts can be used, though SUNPHENON 90LB™ is preferred. SUNPHENON 90LB™ is a decaffeinated extract of green tea leaves (*Camellia sinensis*), which contains greater than about 80 wt. % total polyphenols with about 80 wt. % being catechins. The catechin EGCG is present at greater than about 45 wt. % and the catechin EGC is present at greater than about 8 wt. %.

The green tea extract can be present in an amount from about 2% to about 10%, from about 3% to about 9%, from about 4% to about 8%, from about 5% to about 7% by weight of the composition. In certain examples the green tea extract can be present at about 5.0% (e.g., 5.2%) by weight of the composition.

As noted previously, the disclosed compositions can be used as ingredients of a variety of food products. In some examples, the amount of green tea extract used in the disclosed compositions can be an amount that results in the green tea extract being at from about 50 ppm to about 1000 ppm of the final food product (e.g., granola bar). In some examples, the green tea extract is present in an amount of from about 100 ppm to about 900 ppm, from about 150 ppm to about 850 ppm, from about 200 ppm to about 800 ppm, from about 250 ppm to about 750 ppm, from about 300 ppm to about 700 ppm, from about 350 ppm to about 650 ppm, from about 400 ppm to about 600 ppm, or from about 450 ppm to about 550 ppm of the final food product. For example, the green tea extract can be present in an amount of about 50 ppm, about 100 ppm, about 150 ppm, about 200 ppm, about 250 ppm, about 300 ppm, about 350 ppm, about 400 ppm, about 450 ppm, about 500 ppm, about 550 ppm, about 600 ppm, about 650 ppm, about 700 ppm, about 750 ppm, about 800 ppm, about 850 ppm, about 900 ppm, about 950 ppm, or about 1000 ppm of the final food product, where any of the stated values can form an upper and/or lower endpoint of a range.

Compositions

As described herein, the disclosed compositions contain a powdered preparation comprising PUFAs, as disclosed herein, and powdered green tea extract, as disclosed herein. A method of preparing the disclosed composition includes providing the powdered green tea extract, providing the powdered preparation comprising PUFAs, and blending the two components to form a composition or "blend." The powdered preparation comprising PUFAs and powdered green tea extract can be combined in any order. For example, the microcapsules or emulsions can be added to the powdered green tea extract. Alternatively, the powdered green tea extract can be added to the microcapsules or emulsions. Upon combining the powdered preparation comprising PUFAs with the powdered green tea extract, the components can be mixed or blended to result in the disclosed composition. Such mixing can be accomplished by methods known in the art.

The powdered preparation comprising PUFAs and powdered green tea extract can be combined in a variety of ratios in the disclosed compositions. For example, the disclosed compositions can have a powdered preparation comprising PUFAs to powdered green tea extract weight ratio of 1:10 to 1:50. Other ratios can be used, however, depending on the final use of the disclosed composition, preference, desired loading substance amount, final food product, and the like.

The powdered preparation comprising PUFAs (either microcapsules or emulsion) can comprise about 98%, 97%, 96%, 95%, 94%, 93%, 92%, 91%, or 90% by weight of the composition, where any of the stated values can form an upper or lower endpoint of a range. Likewise, the powdered green tea extract can comprise about 10%, 9%, 8%, 7%, 6%, 5%, 4%, 3%, or 2% by weight of the composition, where any of the stated values can form an upper or lower endpoint of a range. The amount of the powdered preparation comprising PUFAs and the powdered green tea extract are to be selected such that the combination of the two is at least about 90% by weight of the composition.

Additional Components

In the disclosed compositions, one or more antioxidants can be used in combination with or in addition to green tea extract. Such additional components can be present in the disclosed composition at from about 0% to about 10% by weight of the composition. For example, the disclosed compositions can further include citric acid. In preferred aspects, citric acid, when present, can be used in combination with green tea extract rather than as a green tea extract replacement. Citric acid chelates metals such as Fe and Cu, which induce auto-oxidation during storage. Thus, citric acid can prolong the oxidative stability of the disclosed composition and products including the composition, thus allowing the composition and products to be stored for long terms. The citric acid can be present in the disclosed composition in an amount of from about 1% to about 7.5% by weight of the composition. The amount of citric acid can also be expressed in relation to the amount of powdered green tea extract. Thus, in certain examples, the disclosed compositions can contain citric acid and powdered green tea extract in a ratio of 1:1 to 1:5.

Further examples of suitable antioxidants for use as additional components in the disclosed compositions include tocopherols, vitamin E, $CoQ_{10}$, sage extract, rosemary extract, oregano extract, algal extracts, ascorbyl palmitate, ascorbic acid, licopene, hydroxytyrosol, astaxanthin, and synthetic antioxidants (e.g., BHT, BHA, EDTA, TBHQ, ethoxyquin, alkyl gallates, hydroquinones, and tocotrienols).

Methods of Use

Also disclosed herein are food products that comprise the disclosed compositions. Food product refers to any article that can be consumed (e.g., eaten or ingested) by a subject. In some examples, the disclosed compositions can be included in nutritional bars and granola bars. In other examples, the disclosed compositions can be contained in articles such as sachets or shakers, which can be used to mix, pour or sprinkle the disclosed compositions onto and into food products or their ingredients. Still other examples include baked goods (e.g., breads, rolls, cookies, crackers, fruit pies, or cakes), pastas, condiments, salad dressings, soup mixes, snack foods, processed fruit juices, sauces, gravies, syrups, beverages, dry beverage powders, jams or jellies, or pet companion food that have been prepared with a composition as disclosed herein.

The products containing the disclosed compositions can have enhanced sensory and oxidative stabilities, especially as compared to products without the disclosed compositions and with just neat PUFAs or powdered PUFA preparations. The stability of these products can be measured using, for example, a ML Oxipres instrument (Mikrolab Aarhus A/S; Hojbjerg, Denmark). The Oxipres instrument is a rapid predictive tool used to measure qualitatively the oxidative stability of compounds susceptible to oxidation. The measurement is based on consumption of oxygen at elevated temperature and pressure. The induction period (IP) of oxidation is calculated as the time after which the pressure began to decrease abruptly. An increased induction period indicates an improvement in oxidative stability. The induction period of the food products containing the disclosed compositions can be increased by reducing the formation of peroxides or by removing/decomposing the peroxides present in the oil. Thus, the food products prepared using the compositions disclosed herein have longer induction periods due to the use of the compositions as disclosed herein. For example, the disclosed compositions, and products that contain them, can have an induction period of at least about 180 hours, preferably greater than about 185 hours, even more preferable greater than about 190 hours, or most preferably greater than about 195 hours.

Another method for determining the oxidative stability of the food products including the compositions disclosed herein is to utilize a standardized sensory panel. The standardized sensory panel assesses the organoleptic qualities of the composition or food product. The panelists included in these evaluations can select from numeric scales and assign a sensory score to rate the acceptability of the products tested. Specific odor and taste indicators associated with products include acidic, bacony, beany, bitter, bland, burnt, burnt caramel, cardboardy, caramelized, corny, deep fried, fishy, fruity, grains, grassy, green, green tea taste, hay, heated oil, hully, hydrogenated oil, lard, light struck oil, marine, melon, metallic, musty, muted, nutty, oaty, old oats, overheated oil, oxidized, painty, paraffin oil, peanut oil, pecan oil, petroleum, phenolic, pine oil, plastic, pondy, pumpkin, raisins, rancid, raw, reverted oil, rubbery, soapy, sour, stale granola, stale oats, sulfur, sunflower seed shell, sweet, syrupy, tangy, watermelon, waxy, weedy and woody.

The disclosed compositions can be particularly well suited for certain types of food applications. For foods that are enrobed in a coating, e.g., from fat, sugar, and flavor, the oxidative stability of the PUFAs is less of a concern, as is the taste. But foods that are generally porous and that are not enrobed are particularly well suited for using the disclosed compositions. The ingredients of such foods are typically more exposed to oxygen and thus oxygen sensitivity is of greater concern. Further, without an enrobed coating to mask or dominate off flavored ingredients, the presence of off flavored ingredients can be more pronounced and noticed. Thus, creamed fats have been used to enrobe some food products that contain PUFA oils (see WO 2008/24906). Creamed fats typically contain a carrier oil (e.g., palm oil at about 5 to 7 wt. %), an antioxidant, lecithin, and a strong flavor, like bitter sweet chocolate and/or peanut butter. Using the compositions disclosed herein, the stability and sensory qualities of the PUFAs is much increased, and thus they can be used in food products that are not made from, or do not contain, creamed fats. Of course, the disclosed compositions can be used in products that contain strong masking flavors and/or creamed fats; they are however well suited for products that do not contain strong masking flavors and/or creamed fats.

The disclosed compositions and products produced according to the methods disclosed herein can be stored for a prolonged period of time. In some examples, products including the compositions can be stored at ambient temperature for up to 12 months, assuming microbial contamination is minimized. In other examples, products including the disclosed compositions can be stored at 35° C. for 12 weeks, even in the absence of humidity control. The stability of the products upon extended storage can be measured according to the methods disclosed herein, including a sensory panel or an Oxipres instrument.

Products containing the disclosed compositions can have a stability characterized in that the products have a sensory score of less than 3.5, wherein the sensory score is determined by a sensory panel of at least 8 panelists who rate the flavor of the composition on the following scale: "1" means the panelist extremely liked the flavor and described the flavor using terms such as sweet, oaty, bland, syrupy, caramelized, grains, or raisins; "2" means the panelist liked the flavor very much and used terms such as old oats, stale oats, stale granola, burnt caramel, acidic, tangy, or muted; "3" means the panelist liked the flavor and described the flavor as odd, herbal, earthy, mushroom, musty, or green tea-taste; "4" means the panelist was indifferent, choosing terms such as gelatin, metallic, and soapy to describe the flavor; "5" means the panelist disliked the flavor and described the taste as green or grassy; "6" means the panelist disliked the flavor very much and described the taste as fishy or marine; and "7" means the panelist extremely disliked the flavor and described the flavor as painty or rancid. The highest number given for a flavor by each panelist is averaged and the result is the sensory score.

Products containing the disclosed compositions can have a stability characterized in that the products have an induction period of greater than about 180 hours, 185 hours, 190 hours, or 195 hours, as measured by an Oxipress.

By use of the disclosed compositions, products can be prepared that have stability characterized in a passing sensory score (e.g., less than 3.5) and induction period (e.g., >180 hours).

Methods of Preparing Granola Bars

Granola bars containing PUFAs with improved sensory stability can be prepared using the compositions disclosed herein. The granola bars can be flavored or unflavored. The method can include preparing a binding syrup and adding the disclosed composition to the syrup during the cooling stage.

Specifically, ingredients suitable for forming a binding syrup can be mixed and heated. Such ingredients useful for forming a binding syrup include, for example, lecithin, canola oil, high fructose corn sugar, glucose, sugar, water and, optionally, flavoring. The ingredients can be heated to an elevated temperature and held until the appropriate ° Brix is achieved (° Brix=1 g sugar per 100 g $H_2O$). Suitable temperatures at which the ingredients can be mixed include, but are not limited to, at from about 50 to about 150° C., from about 70 to about 140° C., from about 80 to about 130° C., from about 90 to about 120° C., or from about 100 to about 110° C. In other examples, the ingredients can be heated at about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150° C., where any of the stated values can form an upper and/or lower endpoint of a range. In some specific examples, the ingredients can be heated at about 90° C. until the desired ° Brix is achieved (e.g., 85° Brix).

The resulting syrup can then be cooled, at which point different components can optionally be added. For example, citric acid can optionally be added to the binding syrup once the syrup cools to from about 55° C. to about 58° C. The citric acid can be mixed until it is completely dissolved in the binding syrup. Upon further cooling to about 55° C., flavors and/or masking agents can be added to the binding syrup. Suitable flavors and masking flavors include natural flavors (e.g., natural fruit flavors) and artificial flavors (e.g., artificial fruit flavors). For example, the flavors can include mint, menthol, caramel, cinnamon, vanilla, artificial vanilla, chocolate, artificial chocolate, bubblegum, banana, cherry, grape, orange, strawberry, melon, and lemon. Preferred flavors for use in the granola bars disclosed herein include strawberry, caramel, and dark chocolate. In some examples, flavors are not added to the binding syrups that include citric acid.

Upon further cooling, the composition as disclosed herein can be added to the binding syrup. The disclosed composition can be added at a temperature from about 40° C. to 55° C., from about 45° C. to 53° C., or from about 49° C. to 51° C. For example, the disclosed composition can be added at a temperature of about 41° C., about 42° C., about 43° C., about 44° C., about 45° C., about 46° C., about 47° C., about 48° C., about 49° C., about 50° C., about 51° C., about 52° C., about 53° C., about 54° C., or about 55° C., where any of the stated values can form an upper and/or lower endpoint of a range. Preferably, the disclosed composition is added at about 50° C. The resulting binding syrup can then be added into a granola composition and blended until the product is homogenous. The binding syrup can be added to the granola composition at a temperature the same as or lower than the temperature at which the disclosed composition is added to the binding syrup. Suitable ingredients for a granola product include oats, rice crisps, wheat flakes, and mixtures of these. The resulting granola product can be cold-pressed into a bar and further processed.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the disclosed process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Ocean Nutrition Canada Limited (Dartmouth, Canada), Acros Organics (Morris Plains, N.J.), Fisher Scientific (Pittsburgh, Pa.), or Sigma-Aldrich (St. Louis, Mo.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Example 1

Preparation and Storage of Chewy Granola Bar

Flavored and unflavored chewy granola bars were prepared using the ingredients shown in Table 1.

TABLE 1

| | Ingredient | % w/w |
|---|---|---|
| Binding Syrup | Lecithin | 0.110 |
| | Canola oil | 1.10 |
| | HFCS 42 | 7.5 |
| | Glucose syrup | 31.8 |
| | Sugar | 6.5 |
| | Flavor | Q.S. |
| Granola mix | Brown Rice crisp | 7.0 |
| | Rolled oats | 37 |
| | Whole wheat flakes | 9.0 |

Q.S. = Quantities sufficient

The granola bars were prepared by mixing the binding syrup ingredients (i.e., lecithin, canola oil, high fructose corn syrup containing 42% fructose ("HFCS 42" in Table 1), glucose syrup, and sugar) and heating the mixture to 90° C. using a double boiler. The mixture was held at this temperature until 85° Brix was obtained. The resulting syrup was cooled to 55-58° C. For the unflavored bars, citric acid was added at this point and mixed until complete dissolution was achieved. For the flavored bars, flavors (e.g., strawberry, caramel, and dark chocolate) and/or masking agents were added to the bars upon further cooling to 55° C. and mixed until complete dispersion or dissolution was achieved. SUNPHENON 90LB™, a green tea extract (GTE) powder commercially available from Taiyo Kagaku Co. (Yokkaichi, Mie, Japan), and a powdered microencapsulated PUFA from Ocean Nutrition Canada Limited (Dartmouth, Canada), were dry blended together. These were blended together in ratio of powdered green tea extract and powdered microcapsules of 1:20. The resulting composition was then added to the syrup upon cooling to 50° C., and mixed until completely dispersed. No SUNPHENON 90LB™ or powdered microencapsulated PUFA was added to the control bars. After preparing the binding syrup and while at 50° C., the mixture was then added into the granola mix as shown in Table 1 (i.e., brown rice crisp, rolled oats, and whole wheat flakes) and mixed until the sample was homogenous. The mass was sheeted using a 9 in×9 in×0.5 in (23 cm×23 cm×1.3 cm) mold. After sheeting the bar into the mold, the mold and its contents were cooled at 4° C. for 15 to 20 minutes. The sample was removed from the mold, cut to size, and packaged in foiled bags.

The unflavored or flavored chewy granola bars were stored under both accelerated conditions (i.e., 35° C. with no humidity control) and at ambient conditions (i.e., 20-25° C.). Samples under accelerated conditions were evaluated on a weekly basis for 12 weeks and samples under ambient conditions were evaluated monthly for 12 months.

Example 2

Sensory Testing of Chewy Granola Bars

Samples containing a microencapsulated PUFA powder, a powdered green tea extract (SUNPHENON 90LB™), and/or citric acid were prepared as described in Example 1. The microencapsulated PUFA powder contained either 32 mg EPA/DHA per 35 g of powder (data not shown) or 50 mg EPA/DHA per 35 g of powder. SUNPHENON 90LB™ was provided at either 200 ppm or 500 ppm. The amount of citric acid in the samples was 100 ppm or 300 ppm in granolas dosed at 32 mg EPA/DHA. For those granolas dosed at 50 mg EPA/DHA, 300 ppm to 500 ppm of citric acid was tested. The formulations and associated data are provided in FIGS. 1 and 2.

The samples were assessed by a trained panel of eight panelists using a descriptive sensory test where odor and flavor were evaluated on unflavored granola bars. Panelists ranked the flavor acceptability using a hedonic scale. A score of "1" means the panelist extremely liked the flavor and described the flavor using terms such as sweet, oaty, bland, syrupy, caramelized, grains, or raisins. A score of "2" means the panelist liked the flavor very much and used terms such as old oats, stale oats, stale granola, burnt caramel, acidic, tangy, or muted. A score of "3" means the panelist liked the flavor and described the flavor as odd, herbal, earthy, mushroom, musty, or green tea-taste. A score of "4" means the panelist was indifferent, choosing terms such as gelatin, metallic, and soapy to describe the flavor. A score of "5" means the panelist disliked the flavor and described the taste as green or grassy. A score of "6" means the panelist disliked the flavor very much and described the taste as fishy or marine. A score of "7" means the panelist extremely disliked the flavor and described the flavor as painty or rancid.

The highest descriptors weight given by the panelist was used to analyze the data (worse case scenario). The number designated for a descriptor was based on the highest ranking descriptor. For example: a flavor described as bland, earthy, marine would be given a score of 6, whereas a written descriptive as bland, off, earthy, black tea would be given a value of 3. The highest ranking descriptor of all the panelists was averaged. An average score of less than 3.5 is desirable.

The intensity of fishiness flavor was also ranked by the panelists, using the scale of "0" (meaning no fishy flavor) to "6" (meaning a pronounced fishy flavor).

Figure 2:
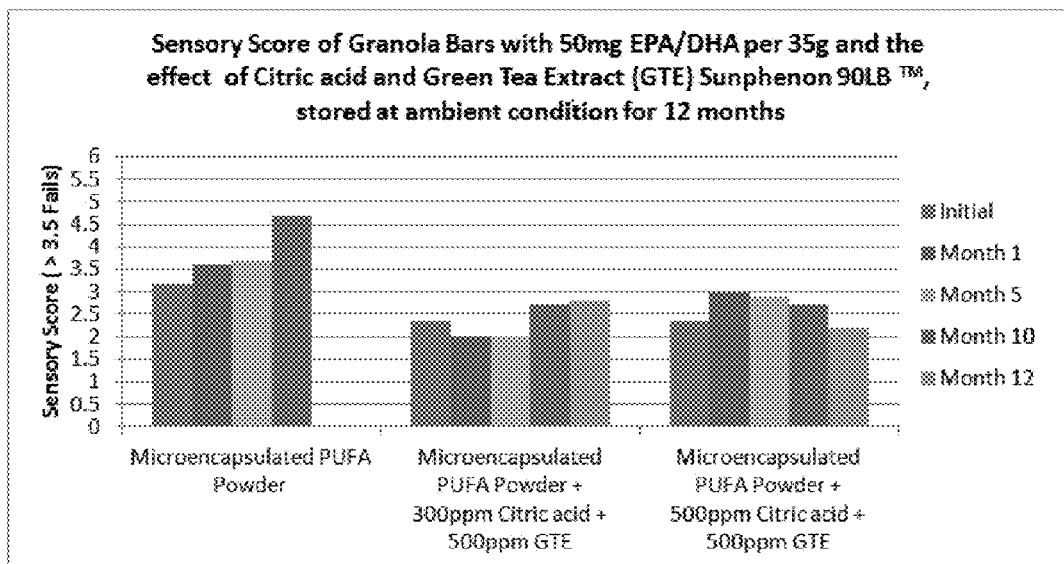
FIG. 2 is graph depicting sensory scores of granola bars prepared with microencapsulated PUFAs (which contained 50 mg EPA/DHA per 35 g of the granola bar) and varying amounts of citric acid and green tea extract after storing under ambient conditions for twelve months. A sensory score of greater than 3.5 is considered failing.

As illustrated in FIGS. 1 and 2, the using a composition containing a green tea extract (SUNPHENON 90LB™ (Taiyo Kagaku Co.; Yokkaichi, Mie, Japan)) and a microencapsulated PUFA powder to form an unflavored cold pressed granola bar improved the sensory stability of the product by reducing detectable fishy notes or off notes related to the microencapsulated PUFA powder. The composition also extended the shelf life of the bar from 4-6 months to 12 months at ambient or 12 weeks at 35° C., with no humidity control.

Example 3

Oxidative Stability Testing of the Chewy Granola Bars

To further confirm the effectiveness of the green tea extract SUNPHENON 90LB™ in minimizing or retarding the oxidative deterioration of the microencapsulated PUFA powder in the granola chewy bar, the oxidative stability was measured using a ML Oxipres (Mikrolab Aarhus A/S; Hojbjerg, Denmark).

Figure 3:
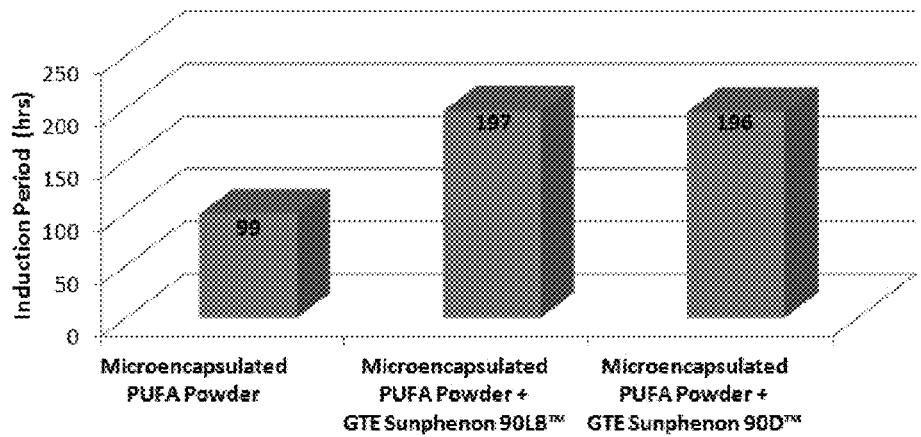
FIG. 3 is a graph illustrating the oxidative stability of granola bars containing microencapsulated PUFAs with and without green tea extract.

A set of experiments was carried out using the unflavored chewy granola bar model system as a vehicle to incorporate the microencapsulated PUFA powder and the powdered green tea extract SUNPHENON 90LB™ and SUNPHENON 90D™ using the same processing conditions described above in Example 1. The experiments were carried out at a temperature of 65° C. for 250 hours in the ML Oxipres. It was found that when the unflavored chewy granola bar only contains the microencapsulated PUFA powder at 50 mg EPA/DHA per serving, the induction period (IP) was 99.0 hours. However, when the unflavored chewy granola bar contained the same microencapsulated PUFA powder plus the addition of 500 ppm of the powdered green tea extract SUNPHENON 90LB™, and SUNPHENON 90D™ the induction period was 197 and 196 hours, respectively (see FIG. 3). These results confirmed the sensory findings provided in Example 2. Using a composition containing the powdered green tea extract SUNPHENON 90LB™ or SUNPHENON 90D™ and a powdered preparation comprising PUFAs in the unflavored model system described above improved the oxidative and sensory stability of the product over time.

Example 4

Sensory Testing of Granola Bars Containing Different Antioxidants

Figure 4:
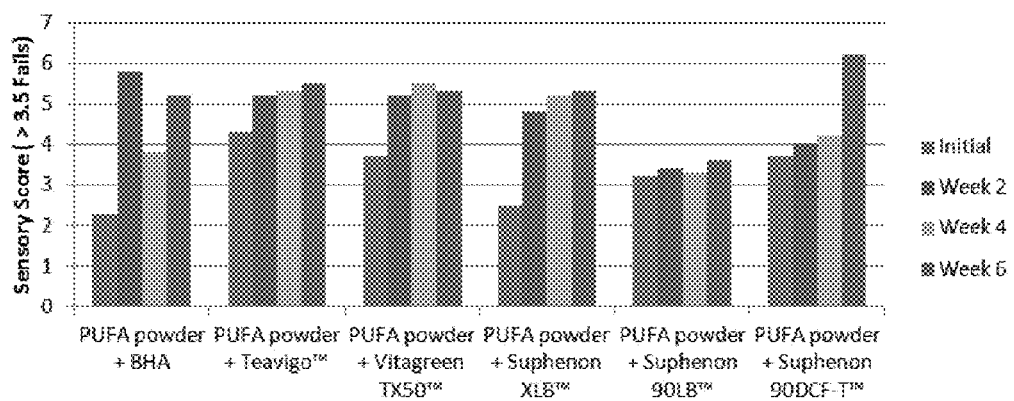
FIG. 4 is a graph depicting sensory scores of granola bars containing microencapsulated PUFAs (which contained 75 mg of EPA/DHA per 35 g of the granola bar) and varying antioxidants, including butylated hydroxyanisole (BHA), TEAVIGO™, VITAGREEN™, SUNPHENON XLB™, SUNPHENON 90LB™, and SUNPHENON 90DCF-T™, over six weeks at 35° C. A sensory score of greater than 3.5 is considered failing.

In order to narrow down the source of the natural antioxidant, a pre-screening was carried out. Granola bars were prepared with formula described in Example 1, except the amounts of microencapsulated PUFA powder and antioxidants were varied. Bars were prepared using a composition containing a microencapsulated PUFA powder (which contained 75 mg of EPA/DHA per 35 g of granola bar) and several sources of green tea extracts such as TEAVIGO™, SUNPHENON 90DCF-T™, GUARDIAN 20S™ and GUARDIAN 20M™ and specific phenolic compounds such as Capros, SABERRY™, Ellagic Extract were tested. As a result, green tea extract sources with high amount of polyphenols such as Teavigo and SUNPHENON 90DCF-T™ show a fair sensory stability, the rest of the natural antioxidants were not sensory stable. To further confirm the previous findings, another set of experiment was carried out. Bars were prepared using a composition containing a microencapsulated PUFA powder (which contained 75 mg of EPA/DHA per 35 g of granola bar and butylated hydroxyanisole (BHA); TEAVIGO™, a green tea extract commercially available from Pharmachem Laboratories, Inc. (Kearny, N.J.); VITAGREEN™ TX50 from Vitiva; SUNPHENON XLB™; SUNPHENON 90LB™; or SUNPHENON 90DCF-T™, green tea extracts commercially available from Taiyo Kagaku Co. The samples were assessed by panelists using the descriptive sensory test described in Example 2. Based on the average of the scores, the granola bars containing a composition with a microencapsulated PUFA powder (labeled as PUFA Powder in FIG. 4) and the green tea extract SUNPHENON 90LB™ provided the best sensory results (see FIG. 4).

Example 5

Sensory Stability Testing of Flavored Granola Bars

Cold pressed, chewy, flavored granola bars were prepared with a microencapsulated PUFA powder and antioxidants, as described in Example 1, except the SUNPHENON 90LB™ green tea extract was varied and citric acid was not used. Specifically, bars were prepared containing 50 mg EPA/DHA per serving, along with 200 to 500 ppm of SUNPHENON 90LB™ green tea extract and one of the following flavors: strawberry, caramel, and dark chocolate. The samples were assessed by panelists using the descriptive sensory test described in Example 2. Based on the average of the scores, the addition of 200 to 500 ppm of the green tea extract to the bars containing microencapsulated PUFA powder improved the sensory stability in reducing detectable fishy notes or off notes related to the microencapsulated PUFA powder ingredient. In addition, the shelf life of the bars was extended from 4-6 months to 12 months at ambient condition (20-25° C.) or 12 weeks under accelerated conditions (35° C.).

Example 6

Effect of Various Antioxidants on the Oxidative Stability of Powdered Microencapsulated PUFAs Granola base were prepare as described in Example 1 using a microencapsulated PUFA powder that contained (50 mg EPA/DHA per 35 g of granola bar) and various natural antioxidants. The results are shown in Table 2. Bars with just the microencapsulated PUFA and no antioxidant had an induction period of 99 hours.

TABLE 2

| Antioxidant | Commercial Name | Composition | Amount | Induction Period (IP) | Senory Score* |
|---|---|---|---|---|---|
| Decaffeinated Green Tea Extract | Sunphenon 90 LB | Total polyphenols 90% Total catechins 80% EGC content 11% EGCG content 50% | 500 ppm | >195 | Pass |
| Decaffeinated Green Tea Extract | Sunphenon 90D | Total polyphenols 90% Total catechins 80% EGC content 12% EGCG content 49% | 500 ppm | >195 | Pass |
| Decaffeinated Green Tea Extract | Sunphenon 90DCF-T | Total polyphenols 80% Total catechins 80% EGC content <1% EGCG content 50% | 500 ppm | >195 | Fail |
| Decaffeinated Green Tea Extract | Sunphenon XLB | Total polyphenols 80% Total catechins 60% EGC content 25% EGCG content 20% | 500 ppm | >195 | Fail |
| Decaffeinated Green Tea Extract | Sunphenon XLB-100 | Total polyphenols 80% Total catechins 60% EGC content 40% EGCG content <1% | 500 ppm | >195 | ND |
| Decaffeinated Green Tea Extract | Sunphenon 80A-T | Total polyphenols 80% Total catechins 70% EGC content <1% EGCG content 55% | 500 ppm | 162 | ND |
| Decaffeinated Green Tea Extract | Teavigo | EGCG content >90% | 500 ppm | 163 | Fail |
| Decaffeinated Green Tea Extract | Prochifar A | Total polyphenols 90 % Total catechins 80% EGC content 12% EGCG content 40% | 500 ppm | 177 | Pass |
| Decaffeinated Green Tea Extract | Prochifar B | Total polyphenols 90% Total catechins 65% EGC content 8% EGCG content 40% | 500 ppm | 172 | ND |
| Decaffeinated Green Tea Extract | Prochifar C | Total polyphenols 90% Total catechins 40% EGC content 9% EGCG content 40% | 500 ppm | 174 | Pass |
| Decaffeinated Green Tea Extract | Prochifar D | Total polyphenols 90% Total catechins 60% EGC content 9% EGCG content 30% | 500 ppm | 181 | ND |
| Decaffeinated Green Tea Extract | Prochifar E | Total polyphenols 90% Total catechins 70% EGC content 9% EGCG content 30% | 500 ppm | 171 | ND |

TABLE 2-continued

| Antioxidant | Commercial Name | Composition | Amount | Induction Period (IP) | Senory Score* |
|---|---|---|---|---|---|
| Decaffeinated Green Tea Extract | Prochifar F | Total polyphenols 90% Total catechins 70% EGC content 9% EGCG content 40% | 500 ppm | 168 | ND |
| Decaffeinated Green Tea Extract | Prochifar G | EGC content 5% EGCG content 10% | 500 ppm | 157 | ND |
| Green Tea Extract | Vitagreen TX50 | Total polyphenols 95% Total catechins 75% EGC content 7% EGCG content 50% | 500 ppm | 169 | Fail |
| Mixture of Green tea extract with other functional ingredients | SyneROX 10 | EGC content 2% EGCG content 10% | 500 ppm | 132 | Pass |
| Green Tea extract powder | Guardian 20S | Total catechins 20% EGC content <1% EGCG content 4% | 500 ppm | 127 | Fail |
| Green Tea extract powder | Guardian 20M | Total catechins 20% EGC content <1% EGCG content 4% | 500 ppm | 130 | Fail |
| Black Currant Extract Powder | Ginnovay Black Currant Extract | *Ribes nigrum* L 10% | 500 ppm | 110 | ND |
| Natural Astaxanthin powder | AstaReal P2AF | Astaxanthin 2% | 10 ppm | 103 | ND |
| *Origanum Vulgare* of Labiatae Family | Origanox WS | Rosemarinic acid, Quercetin and their derivatives | 300 ppm | 91 | ND |
| *Melissa Offcinalis* of Labiatae Family | Origanox WS-LB | Rosemarinic acid and their derivatives | 300 ppm | 88 | ND |
| Hytolive powder | Hytolive powder | Hydroxytyrosol 14.03%, Tyrosol 2%, other phenolics 1.75% | 100 ppm | 103 | ND |
| Aquaolive | Aquaolive | Hydroxytyrosol >9%, Ascorbic acid 4%, Mixed tocopherols 4% | 130 ppm | 126 | ND |
| Hytolice syrup 35% | Hytolice syrup 35% | Hydroxytyrosol 42%, Tyrosol 5.63%, other phenolics 0.10% | 70 ppm | 128 | ND |
| Grape seed extract | Orac-15,000 Grape Extract | Polyphenols 80%. ORAC value: 15,000 | 300 ppm | 104 | ND |
| Fruit extract Blend | Standardized Fruit Blend (FSB) | Polyphenols 40% (Grape, pomegranate, blueberry, chokeberry, mangosteen, cranberry, Goji berry, apple and bilberry) ORAC value: 7,500 | 500 ppm | 126 | ND |
| Grape Extract *Vitis vinifera* I., *Carignane*, *Cinsault* | BioVin Full Spectrum | Proanthocyanidisn 95%, Total Poliphenols 75%, Trans-Resveratrol > 200 ppm | 300 ppm | 103 | ND |
| Grape Extract *Vitis vinifera* I | BioVin ™ 20 | Polyphenols 20%, Anthocyanins 4-6% | 500 ppm | 102 | ND |

*ND is "not determined." Pass had a sensory score below 3.5 and fail had a sensory score of 3.5 or above.

Various sources of natural antioxidants were assessed in their effectiveness for minimizing or retarding the oxidative deterioration of the powdered microencapsulated PUFA. In this qualitative test measured by Oxipres, a higher induction time of greater than about 195 hours, indicates an excellent improvement in oxidative stability of the powdered microencapsulated PUFA by the natural antioxidant. Lower induction time, e.g., less than about 180 hours, indicates poor performance of the natural antioxidant over the oxidative stability of the powdered microencapsulated PUFA. Sunphenon 90LB™ or Sunphenon 90D™ showed an excellent induction period over time. Other Sunphenon green tea extracts, 90 DCF-t and XLB, had poor sensory performance even though they had a successful induction period. While not wishing to be bound by theory, it is believed that the poor sensory scores were the result of low amounts of EGC (for 90DCF-T) or EGCG (for XLB), or the ratio of EGC to EGCG.

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods and combinations of various features of the compositions and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A powder blend composition, comprising: a homogenous blend of a powdered green tea extract (GT powder) and a powdered preparation comprising polyunsaturated fatty acids (PUFA powder), wherein the combined amount of the GT powder and the fatty acids PUFA powder is at least about 90% by weight of the composition, wherein the weight ratio of the GT powder and the powdered PUFA powder is from 1:50 to 1:10, wherein the GT powder comprises a total polyphenol content of less than 95 wt. % based on the weight of the GT powder, with at least 40 wt. % of epigallocatechin gallate (EGCG) based on the weight of the GT powder and from about 5 to about 20 wt. % of epigallocatechin (EGC) based on the weight of the GT powder.

2. The composition of claim 1, wherein the PUFA powder comprises a microcapsule.

3. The composition of claim 1, wherein the PUFA powder comprises a powdered emulsion.

4. The composition of claim 1, wherein the GT powder contains greater than about 80 wt. % total polyphenols and an EGCG content of greater than 45 wt. % based on the weight of the GT powder.

5. The composition of claim 1, wherein the GT powder contains greater than about 80 wt. % total polyphenols, an EGCG content of from about 45 to about 55 wt. %, and a EGC content of from about 10 to about 13 wt. % based on the weight of the GT powder.

6. The composition of claim 1, wherein the GT powder contains an epicatechin (EC) content of from about 6 to about 15 wt. % based on the weight of the GT powder.

7. The composition of claim 2, wherein the microcapsule comprises an agglomeration of primary microcapsules and a loading substance, each individual primary microcapsule having a primary shell, wherein the loading substance comprises a polyunsaturated fatty acid and is encapsulated by the primary shell, and wherein the agglomeration is encapsulated by an outer shell.

8. The composition of claim 7, wherein the primary shell, the outer shell, or both the primary and outer shells comprise a surfactant, gelatin, polyphosphate, polysaccharide, or a mixture thereof.

9. The composition of claim 7, wherein the primary shell, the outer shell, or both the primary and outer shells comprise any one or more of the following proteins: gelatin type A, gelatin type B, pork gelatin, beef gelatin, fish gelatin, kosher gelatin, non-kosher gelatin, Halal gelatin, non-Halal gelatin, milk protein, casein, caseinate, whey protein, soy protein, pea protein, rice protein, canola protein, albumin, alfa-lactalbumin, beta-lactoglobumin, or ovalbumin, in combination with any one or more of the following polymers: polyphosphate, gum arabic, gellan gum, xylan gum, agar, alginate, chitin, chitosan, carrageenan, pectin, starch, modified starch, polysorbiton, maltodextrin, cyclodextrin, cellulose, methyl cellulose, ethyl cellulose, hydropropylmethylcellulose, or carboxymethylcellulose.

10. The composition of claim 7, wherein the primary shell, the outer shell, or both the primary and outer shells comprise fish gelatin, pork gelatin, or beef gelatin.

11. The composition of claim 7, wherein the primary shell, the outer shell, or both the primary and outer shells comprise a complex coacervate.

12. The composition of claim 7, wherein the complex coacervate is a complex coacervate of gelatin and polyphosphate.

13. The composition of claim 7, wherein the outer shell has an average diameter of from about 1 μm to about 2,000 μm.

14. The composition of claim 7, wherein the primary shell has an average diameter of from about 40 nm to about 10 μm.

15. The composition of claim 7, wherein the loading substance is from about 20% to about 90% by weight of the microcapsule.

16. The composition of claim 3, wherein the emulsion comprises a polymer component and a loading substance comprising a polyunsaturated fatty acid.

17. The composition of claim 16, wherein the polymer component comprises a surfactant, gelatin, polyphosphate, polysaccharide, or a mixture thereof.

18. The composition of claim 16, wherein the polymer component comprises any one or more of the following: gelatin type A, gelatin type B, pork gelatin, beef gelatin, fish gelatin, kosher gelatin, non-kosher gelatin, Halal gelatin, non-Halal gelatin, milk protein, casein, caseinate, whey protein, soy protein, pea protein, rice protein, canola protein, albumin, alfa-lactalbumin, beta-lactoglobumin, ovalbumin, polyphosphate, gum arabic, gellan gum, xylan gum, agar, alginate, chitin, chitosan, carrageenan, pectin, starch, modified starch, polysorbiton, maltodextrin, cyclodextrin, cellulose, methyl cellulose, ethyl cellulose, hydropropylmethylcellulose, and carboxymethylcellulose, including any mixture or combination of these.

19. The composition of claim 16, wherein the polymer component comprise fish gelatin, pork gelatin, or beef gelatin.

20. The composition of claim 16, wherein the emulsion contains an average droplet size of less than about 1000 nm.

21. The composition of claim 16, wherein the loading substance is from about 1% to about 50% by weight of the emulsion.

22. The composition of claim 7, wherein the loading substance comprises one or more oils chosen from a microbial oil, algal oil, fungal oil, and plant oil.

23. The composition of claim 7, wherein the loading substance comprises fish oil.

24. The composition of claim 7, wherein the loading substance comprises an omega-3 fatty acid, an ester of an omega-3 fatty acid, and/or a mixture thereof.

25. The composition of claim 24, wherein the ester of an omega-3 fatty acid comprises an alkyl ester of an omega-3 fatty acid, a monoglyceride of an omega-3 fatty acid, a diglyceride of an omega-3 fatty acid, a triglyceride ester of an omega-3 fatty acid, a phytosterol ester of an omega-3 fatty acid, an ester of an omega-3 fatty acid and an antioxidant, a furanoid ester of an omega-3 fatty acid, and/or a mixture thereof.

26. The composition of claim 7, wherein the loading substance comprises docosahexaenoic acid and/or eicosapentaenoic acid, a C1-C6 alkyl ester thereof, a triglyceride ester thereof, a phytosterol ester thereof, and/or a mixture thereof.

27. The composition of claim 7, wherein the loading substance further comprises one or more of vitamin A, vitamin D, vitamin E, and vitamin K, tocotrienol, lycopene, lutein, astaxanthin, zeazanthin, phytosterol or esters thereof, stanol or and esters thereof, Coenzyme Q 10, ubiquinol, a hydrophobic amino acid, or an essential oil.

28. The composition of claim 7, wherein the loading substance further comprises an additional biologically active substance or a nutritional supplement.

29. The composition of claim 1, further comprising citric acid.

30. A food product comprising the composition of claim 1.

31. The food product of claim 30, wherein the food product is a nutritional bar.

32. The food product of claim 30, wherein the food product is a granola bar.

33. A method for preparing the composition of claim 1, comprising: blending the powdered green tea extract and the powdered preparation comprising polyunsaturated fatty acids to form the powder blend composition of claim 1.

34. A method for preparing a granola bar, comprising: providing a binding syrup at an elevated temperature; cooling the binding syrup; optionally adding citric acid to the cooled binding syrup; optionally adding a flavor, a masking flavor, or a mixture of these to the cooled binding syrup; adding the powder blend composition of claim 1; and blending the resulting mixture with a granola composition.

35. The method of claim 34, wherein the citric acid is present in an amount of from 1 to 7.5% by weight of the powder blend composition of claim 1 comprising the powdered green tea extract and the powdered preparation comprising polyunsaturated fatty acids.

\* \* \* \* \*